United States Patent [19]
Robin

[11] Patent Number: 4,983,762
[45] Date of Patent: Jan. 8, 1991

[54] PREPARATION OF BIURETO POLYISOCYANATES

[75] Inventor: Jean Robin, Lyon, France

[73] Assignee: Rhone-Poulenc Chimie de Base, Courbevoie, France

[21] Appl. No.: 512,604

[22] Filed: Apr. 23, 1990

Related U.S. Application Data

[63] Continuation of Ser. No. 262,188, Oct. 20, 1988, abandoned, which is a continuation of Ser. No. 946,197, Dec. 24, 1986, abandoned.

[30] Foreign Application Priority Data

Jul. 4, 1986 [FR] France ............................... 86 09947

[51] Int. Cl.$^5$ ........................................... C07C 273/00
[52] U.S. Cl. ..................................................... 560/335
[58] Field of Search ......................................... 560/335

[56] References Cited

U.S. PATENT DOCUMENTS 4,218,390 8/1980 Brusilovsky et al. ............... 560/335

Primary Examiner—Alan Siegel
Attorney, Agent, or Firm—Burns, Doane, Swecker & Mathis

[57] ABSTRACT

Clear, precipitate-free, storage-stable biureto polyisocyanates, well adopted for paint applications, are prepared by reacting at least one aliphatic, alicyclic or arylaliphatic monomeric diisocyanate with water, at a temperature of at least 70° C. and under an absolute pressure of at least 1.2 bar, including a partial pressure of carbon dioxide of at least 0.2 bar.

13 Claims, No Drawings

PREPARATION OF BIURETO POLYISOCYANATES

This application is a continuation of application Ser. No. 07/262,188, filed Oct. 20, 1988 now abandoned, which is a continuation of application Ser. No. 06/946,197, filed Dec. 24, 1986 now abandoned.

BACKGROUND OF THE INVENTION

1. Field of the Invention

The present invention relates to the preparation of a polyisocyanate containing a biuret group, and, more especially, to the preparation of such biureto polyisocyanate from an aliphatic, alicyclic or arylaliphatic diisocyanate and water.

2. Description of the Prior Art

Polyisocyanates containing a biuret group are useful in the production of foams, adhesives and paints.

Among these applications, the use of such polyisocyanates as constituents of paints is becoming increasingly important, especially in the automotive industry.

Paint films made of aromatic polyisocyanates are known to turn yellow and crack.

On the other hand, films and paints made from aliphatic, alicyclic or arylaliphatic polyisocyanates retain their properties for very long periods of time and are therefore particularly suitable for motor vehicles.

However, the preparation of aliphatic, alicyclic and arylaliphatic polyisocyanates from a diisocyanate and water, presents certain disadvantages.

Thus, according to U.S. Pat. Nos. 3,124,605 and 3,902,127, the reaction of the monomeric diisocyanate with water produces polyurea, which precipitates. The reaction between the monomeric diisocyanate and the water, which dissolves in small amounts in the diisocyanate, produces the polyisocyanate containing a biuret group. However, the reaction of water with the small amounts of monomeric diisocyanate which it is capable of dissolving results in the polyurea.

In published French Application No. 2,382,468, it has been proposed to solve this problem by preparing these polyisocyanates by reacting the monomeric diisocyanate with water, at a temperature of at least 70.C and in a mixture of an ethylene glycol derivative, such as ethylene glycol acetate methyl ether, and a methyl or ethyl phosphate.

This process enables the precipitation of the polyurea in the polyisocyanate to be virtually eliminated.

However, it has the disadvantage of requiring large amounts of solvent, and this greatly reduces the production capacity of the apparatus and complicates subsequent distillation operations.

SUMMARY OF THE INVENTION

Accordingly, a major object of the present invention is the provision of an improved process for the preparation of polyisocyanates containing a biuret group in which the disadvantages and drawbacks of the prior art are virtually eliminated.

Briefly, the present invention features reacting at least one aliphatic, alicyclic or arylaliphatic monomeric diisocyanate with water, the subject reaction being carried out at a temperature at least equal to 70° C. and at an absolute pressure at least equal to 1.2 bar, including a partial pressure of carbon dioxide at least equal to 0.2 bar.

DETAILED DESCRIPTION OF THE PREFERRED EMBODIMENTS OF THE INVENTION

More particularly according to the present invention, it is envisaged to utilize either a pressure, equal to atmospheric pressure, of a gas which is unreactive towards the reactants, such as nitrogen, argon or air, in a dry state, supplemented by a partial pressure of carbon dioxide which is equal to or greater than 0.2 bar, or to carry out a purge with carbon dioxide and to utilize an initial pressure equal to or greater than 1 bar absolute.

The autogenous pressure of the reaction, due to the formation of carbon dioxide, ;:ay be permitted to increase throughout the reaction, or may be maintained at the desired value by permitting a proportion of the $CO_2$ formed to escape.

Although the use of very high pressures is hardly of practical interest, the process according to the invention can be used at carbon dioxide partial pressures of 0.2 to 100 bars.

However, the partial pressure of the carbon dioxide preferably ranges from 0.5 to 50 bars, the total pressure being greater than or equal to 1.5 bar absolute.

The monomeric diisocyanates which are advantageously used in the process of the present invention are aliphatic diisocyanates, alicyclic diisocyanates and arylaliphatic diisocyanates, the isocyanate groups of which are not directly linked to an aromatic ring.

The following are representative of such monomeric diisocyanates, without limitation:

1,3-diisocyanatopropane,
1,4-diisocyanatobutane,
1,5-diisocyanatopentane,
1,6-diisocyanatohexane,
1,4-diisocyanato-2-ethylbutane,
1,5-diisocyanato-2-methylpentane,
1,6-diisocyanato-2,2,4-trimethylhexane,
1,6-diisocyanato-2,4,4-trimethylhexane,
1,2-diisocyanatocyc.o-hexane,
1,4-diisocyanatocyclohexane,
1,2-bis(isocyanatomethyl)cyclobutane,
bis(4-isocyanatocyclohexyl)methane,
3,3,5-trimethyl-5-isocyanatomethyl-1-isocyanatocyclohexane,
1,4-bis(isocyanatomethyl)benzene, and
1,2-bis(isocyanatomethyl)benzene.

The monomeric diisocyanates may be used separately, or in any admixture thereof.

Thus, for example, 1,6-diisocyanatohexane, which is one of the preferred monomeric diisocyanates, may be used by itself or mixed, especially with 1,5-diisocyanato-2-methylpentane and/or 1,4-diisocyanato-2-ethylbutane; mixtures of the latter two diisocyanates may also be used.

The molar ratio of monomeric diisocyanate to water may vary over very wide limits. However, the molecular weight of the polyisocyanate produced is proportionately higher, the lower the molar ratio of monomeric diisocyanate to water. In general, it is not advantageous to utilize a molecular weight and a viscosity which are too high.

Furthermore, the molecular weight and the viscosity of the polyisocyanate produced are proportionately lower, the higher the ratio of monomeric diisocyanate to water. However, an excessively high ratio is of no economic interest, since it involves the separation and the recovery of a large amount of monomeric diisocyanate.

Accordingly, a molar ratio of monomeric diisocyanate to water of from 2 to 40 is preferably selected. This ratio more preferably ranges from 5 to 15.

The temperature at which the reaction of the monomeric diisocyanate with water is carried out typically ranges from 70 C to 200.C. Use of a higher temperature does not interfere with the reaction, but gives rise to undesirable discolorations.

The process is preferably carried out at from 110° C. to 150° C.

The process according to the invention may be carried out in the presence or in the absence of solvent.

When it is carried out without using any solvent, the agitation must be sufficient to produce good contact between the monomeric diisocyanate and the water.

The results obtained are highly satisfactory; the biuret obtained is clear.

In another embodiment of the invention, small amounts of solvent are used to dilute the water and to promote its contact and hence its reaction with the monomeric diisocyanate.

By "small amounts of solvent" are intended amounts representing from 1 to 10 times the weight of the water employed. These amounts preferably represent from 1 to 5 times the weight of the water employed. The values of these FIGURES are only intended as a guide, because it is also possible to carry out the reaction in a solvent medium, that is to say, for example, with an amount of solvent representing from 10% to 80% by weight of the reaction mixture, without creating any problem.

The results obtained in a solvent medium are excellent, but, obviously, are again accompanied by the disadvantage associated with a lower production capacity of the apparatus and the need for additional separation operations.

When it is present in a small amount or in a larger amount, the solvent may be an alkoxyalkane or an alkoxyalkane carboxylate derived, for example, from ethylene glycol (or from ethylene oxide), from propylene glycol (or from propylene oxide) and, if desired, from a carboxylic acid such as acetic acid.

The ethylene glycol derivatives described in the aforenoted published French Application No. 2,382,468 are exemplary.

More particularly representative are 2-methoxyethyl acetate, 1,2-dimethoxyethane, 2-ethoxyethyl acetate, ethylene glycol diacetate, 1-methoxy-2-propyl acetate, 2-methoxy-1-propyl acetate, 1-ethoxy-2-propyl acetate or 2-ethoxy-1-propyl acetate.

The solvent used may also be a methyl and/or ethyl ester of phosphoric acid, especially trimethyl phosphate, triethyl phosphate, dimethyl ethyl phosphate or diethyl methyl phosphate.

When used, these solvents can be employed separately or as mixtures, such as, for example, mixtures of an alkoxyalkane or an alkoxyalkane carboxylate with a phosphoric ester.

In practice, the process according to the invention may be carried out by first charging the monomeric diisocyanate or the mixture of diisocyanates; the apparatus is purged with a dry inert gas such as nitrogen or argon or with carbon dioxide. Water, diluted with 1 to 10 times its weight of one of the solvents indicated above, is then added.

The apparatus is pressurized to 2 to 10 bars absolute using carbon dioxide and heated to about 120° C. to 140° C. The pressure is generally maintained at a value of 2 to 10 bars absolute by the removal of excess $CO_2$.

When the reaction is complete (a few minutes to several hours), carbon dioxide is stripped off and excess monomeric diisocyanate is removed. A clear, precipitate-free biuret is obtained. Its viscosity is a function of the selected molar ratio of diisocyanate to water.

The biuret is stable over time; no precipitation is observed after several months of storage, nor is any appreciable increase in the free diisocyanate content.

In order to further illustrate the present invention and the advantages thereof, the following specific examples are given, it being understood that same are intended only as illustrative and in nowise limitative.

EXAMPLES 1 TO 5

1,6-Diisocyanatohexane (HDI) and, if desired, solvents, were charged into a 3.6 liter autoclave fitted with a helical stirrer and heated by means of a circulation jacket.

Water was injected into the HDI by means of a metering pump having an output which could be adjusted from 0 to 600 ml/hr and which was connected to a dip tube. The gas formed escaped through a reflux condenser, the top of which was equipped with a manometer and an adjustable calibrated valve enabling the autoclave to be maintained at a previously selected constant pressure.

HDI was heated (with the solvents, if desired) to 130° C. and water was added at a constant rate of 1 ml/min. After the required amount had been added, the temperature was maintained at 130.C for 3 hours.

Essentially upon completion of the addition of the water, the pressure increased and reached the selected value. The adjustable valve then opened, permitting excess gas to escape and maintained the autoclave at the selected test pressure.

Upon completion of the operation, the autoclave was restored to atmospheric pressure, was cooled and the product obtained, a mixture of HDI, biuret and, if desired, solvents, was drained.

This product was then evaporated by means of a stirred film evaporator.

The data and the results of the various examples are reported in the Table below:

TABLE

| | Example 1 | Example 2 | Example 3 | Example 4 | Example 5 |
|---|---|---|---|---|---|
| HDI | 1508 g | 2262 g | 2262 g | 2262 g | 2262 g |
| Water | 20 g | 30 g | 30 g | 30 g | 30 g |
| Solvents (1) | 650 g | — | — | — | — |
| Absolute pressure | 6 bars | 6 bars | 4 bars | 2 bars | 1.3 bar |
| Viscosity of the biuret at 25° C. | 8.9 Pa.s | 4.2 Pa.s | 3.6 Pa.s | 3.3 Pa.s | 4.3 Pa.s |
| % HDI by weight upon completion of the test | * 0.05 | * 0.05 | * 0.05 | * 0.05 | * 0.05 |

TABLE-continued

| | Example 1 | Example 2 | Example 3 | Example 4 | Example 5 |
|---|---|---|---|---|---|
| Stability (2) % HDI by weight | 0.2 | 0.2 | 0.2 | 0.2 | 0.2 |

(1) = mixture of equal weights of methoxyethyl acetate and ethyl phosphate
(2) = after one month of storage at 60° C.
(*) = limit of the accuracy of determination.

It was determined that when the operation was carried out without solvent the biuret obtained was less viscous (Example 2) than when the operation was carried out with solvents (Example 1).

In all of the examples, the product obtained upon completion of the reaction and the final biuret were clear.

COMPARATIVE EXAMPLE A

When the biuretization reaction was carried out under the same conditions as in Examples 2 to 5 (without solvent), but at atmospheric pressure, the product obtained was very cloudy and polyurea had precipitated.

% HDI by weight upon completion of the test: 0.15%;

% HDI by weight after one month of storage at 60° C.: 0.8%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a biureto polyisocyanate, comprising reacting at least one aliphatic, alicyclic or arylaliphatic monomeric diisocyanate with water, at a temperature of at least 70° C. and under an absolute pressure of at least 1.2 bar, including a partial pressure of carbon dioxide of at least 0.2 bar, wherein said water is introduced into the reaction zone to said diisocyanate in liquid form and wherein said water is at least partially in liquid form during the biuretization reaction.

2. The process as defined by claim 1, wherein the partial pressure of carbon dioxide ranges from 0.5 to 50 bars and the absolute pressure is at least 1.5 bar.

3. The process as defined by claim 1, wherein the molar ratio of monomeric diisocyanate to water ranges from 2 to 40.

4. The process as defined by claim 1, carried out in the absence of solvent.

5. The process as defined by claim 1, carried out in the presence of at least one reaction solvent.

6. The process as defined by claim 5, said at least one reaction solvent comprising an alkoxyalkane, an alkoxyalkane carboxylate, or a methyl and/or ethyl ester of phosphoric acid.

7. The process as defined by claim 5, the amount by weight of said solvent ranging from 1 to 10 times the weight of the water.

8. The process as defined by claim 5, the amount by weight of said solvent ranging from 10 to 80% of the weight of the reaction mixture.

9. The process as defined by claim 6, said at least one reaction solvent comprising 2-methoxyethyl acetate, 1,2-dimethoxyethane, 2-ethoxyethyl acetate, ethylene glycol diacetate, 1-methoxy-2-propyl acetate, 2-methoxy-1-propyl acetate, 1-ethoxy-2-propyl acetate, 2-ethoxy-1-propyl acetate, trimethyl phosphate, triethyl phosphate, dimethyl ethyl phosphate, or diethyl methyl phosphate.

10. The process as defined by claim 1, carried out at a temperature of from 70° C. to 200° C.

11. The process as defined by claim 3, said molar ratio ranging from 5 to 15.

12. The process as defined by claim 7, the amount by weight of said solvent ranging from 1 to 5 times the weight of the water.

13. The process as defined by claim 1, said at least one monomeric diisocyanate comprising 1,3-diisocyanatopropane, 1,4-diisocyanatobutane, 1,5-diisocyanatopentane, 1,6-diisocyanatohexane, 1,4-diisocyanato-2-ethylbutane, 1,5-diisocyanato-2-methylpentane, 1,6-diisocyanato-2,2,4-trimethylhexane, 1,6-diisocyanato-2,4,4-trimethylhexane, 1,2-diisocyanatocyclohexane, 1,4-diisocyanatocyclohexane, 1,2-bis(isocyanatomethyl)cyclobutane, bis(4-isocyanatocyclohexyl)methane, 3,3,5-trimethyl-5-isocyanatomethyl-1-isocyanatocyclohexane, 1,4-bis(isocyanatomethyl)benzene, or 1,2-bis(isocyanatomethyl)benzene.

* * * * *